United States Patent [19]
Nelson

[11] Patent Number: 5,833,638
[45] Date of Patent: Nov. 10, 1998

[54] BACK BRACE

[76] Inventor: Ronald E. Nelson, 1120 Second St., Box 441, Chetek, Wis. 54728

[21] Appl. No.: 661,074

[22] Filed: Jun. 10, 1996

[51] Int. Cl.[6] ....................................................... A61F 5/37
[52] U.S. Cl. ............................................. 602/19; 129/96.1
[58] Field of Search ................................ 602/19; 450/94, 450/98, 112, 131, 132

[56] References Cited

U.S. PATENT DOCUMENTS

| | | |
|---|---|---|
| 605,299 | 6/1898 | Perrottet . |
| 929,179 | 7/1909 | Wood . |
| 1,367,420 | 2/1921 | Munter . |
| 2,793,368 | 5/1957 | Nouel . |
| 3,434,469 | 3/1969 | Swift . |
| 3,554,190 | 1/1971 | Kaplan . |
| 4,175,553 | 11/1979 | Rosenberg . |
| 4,572,167 | 2/1986 | Brusnwick . |
| 4,627,109 | 12/1986 | Carabelli et al. . |
| 4,833,730 | 5/1989 | Nelson . |
| 5,040,524 | 8/1991 | Votel et al. . |
| 5,148,549 | 9/1992 | Sydor . |
| 5,176,131 | 1/1993 | Votel et al. . |
| 5,241,704 | 9/1993 | Sydor . |
| 5,257,419 | 11/1993 | Alexander . |
| 5,437,617 | 8/1995 | Heinz et al. ............................... 602/19 |

*Primary Examiner*—Jerome Donnelly
*Attorney, Agent, or Firm*—Burd, Bartz & Gutenkauf

[57] ABSTRACT

A back brace for providing back support to the lumbar region of a wearer. The back brace includes a band that wraps around the torso region of a person in covering relationship to the region of the iliac crests. The base has accommodation panels attached to it that cover the iliac crest regions and accommodate the protuberance thereof in order to provide a better fit on the body. In one embodiment, the base includes an elastic band and the panels are of an inelastic material. In another embodiment, the brace includes a waist band that is of an inelastic material, and the accommodation panels covering the iliac crests are formed of an elastic material.

8 Claims, 4 Drawing Sheets

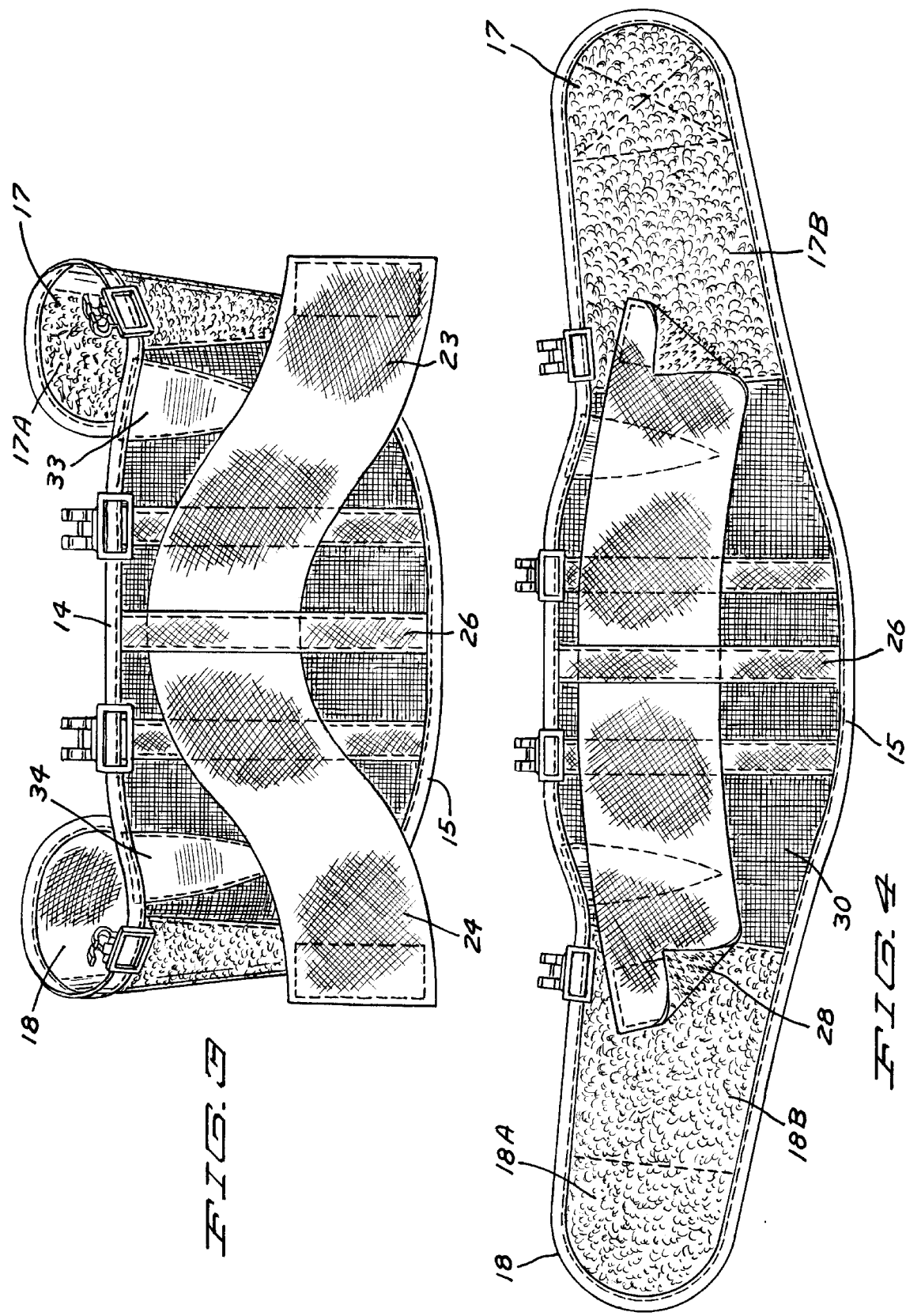

BACK BRACE

BACKGROUND OF THE INVENTION

The present invention relates to a back support or brace for use by an individual engaging in relatively strenuous endeavor utilizing back muscles.

The small of the back or the lumbar region accommodates the largest muscle group in the human body. These vital muscles are used for practically all activity, such as walking, running, standing, sitting, lifting and throwing. Injury to these muscles can, in one form or another, significantly compromise an individual's daily activity whether through disability or discomfort. Protection of these muscles is needed to prevent injury, prevent aggravation to preexistent injury, allow healing of an injury and in some instances to correct an abnormality.

Back braces are presently used as the most common form of protection to this region. Many of these take the form of a simple wrap extended around the torso. Some are elastic, some are inelastic, and some are a combination of the two. Most involve a relatively wide base that wraps around the torso and fastens in the front. It is important that the base conform to the small of the back in order to provide proper support and stay in position on the back. The pelvic structure of an individual can interfere with this objective. The base should compress the torso to provide compressive force to the small of the back. The base spans the hip bones on either side of the body. The two iliac bones form the outer extremities of the pelvic structure. The crest of the ilium or hip bone is problematic. The rest of the torso yields to pressure upon tightening of the base. The ilium does not yield. With prior art braces the greatest amount of pressure tends to be imposed upon the region of the ilium and limits the amount of pressure imposed upon the sacral region of the back. The base tends to hang up on the hip bone. This inhibits conformance to the back. It also results in the base riding up on the back.

SUMMARY OF THE INVENTION

The invention comprises a back brace to provide improved support to the lower lumbar region of the back. The brace includes a base having a band that wraps snugly around the torso with a top edge encircling the waist and a lower edge that encircles the body so as to encompass the small of the back. The base has panels on either side that are positioned over the regions of the crest of the ilium. The panels accommodate for the iliac protuberances. This permits the rear portion of the brace to conform to the small of the back and inhibits the base from riding up in the back. Each panel is substantially triangular in shape. One side of the triangle is coextensive with a segment of the top edge of the base. The apex of the triangle is directed downwardly. In one form of the invention, the base is formed of an inelastic material, and the accommodating panels are formed of an elastic material. The elastic stretches over the crest of the ilium to compensate for the additional expanse that must be covered by the base and that would otherwise cause a slack area at the small of the back. In another form of the invention, the base is formed of an elastic material and the panels are formed of an inelastic material. The panels again compensate for the added dimension of the ilium. In each case the base fits better and does not tend to ride up.

IN THE DRAWINGS

FIG. 3 is a back view of the back brace of FIGS. 1 and 2 removed from the human torso;

FIG. 4 is back view like that of FIG. 3 with the brace spread flat for purposes of illustration;

DESCRIPTION OF PREFERRED EMBODIMENTS

Figure 1:
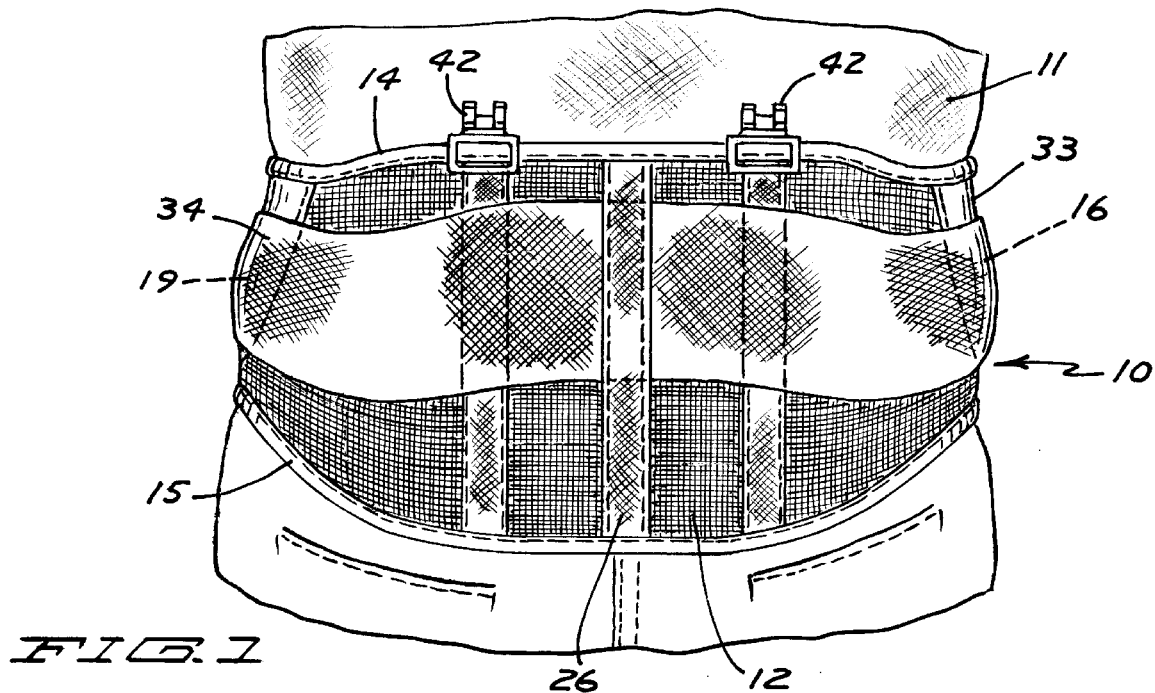
FIG. 1 is a rear elevational view of a back brace according to one form of the invention installed upon a human torso.
Figure 2:
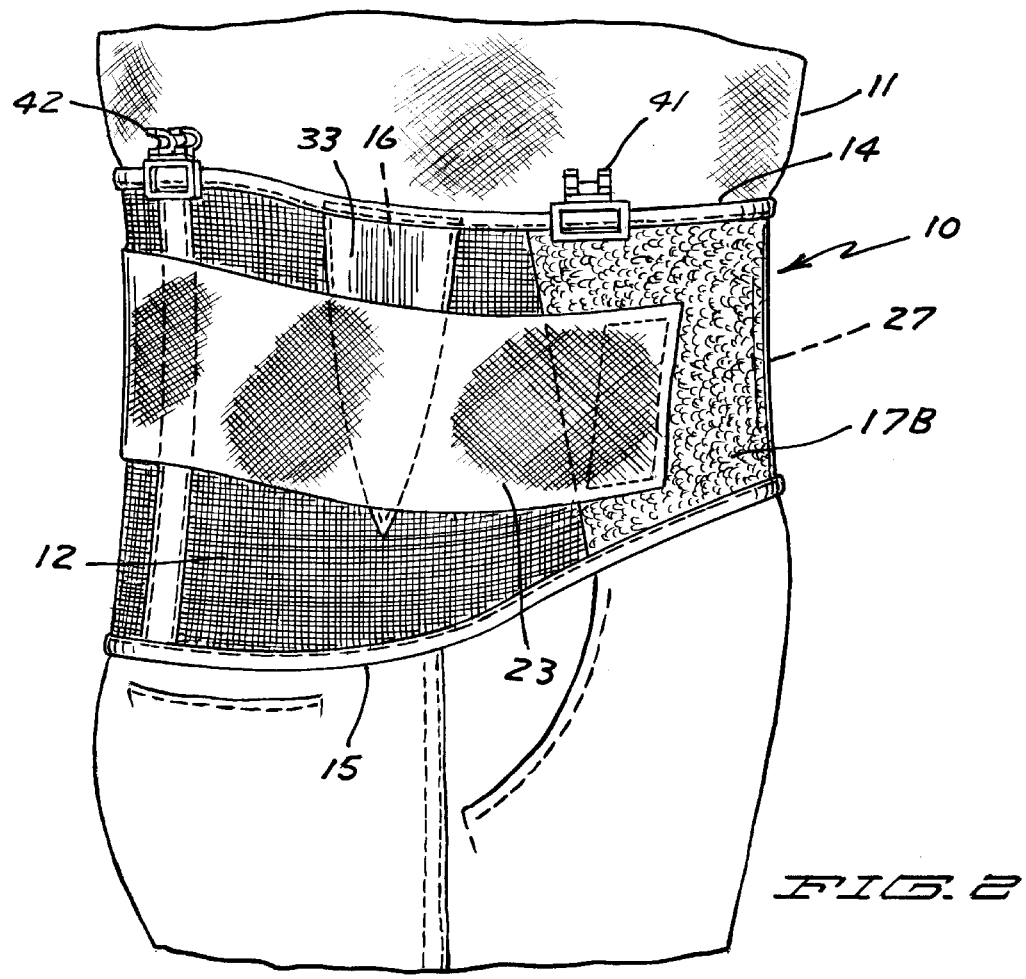
FIG. 2 is a right side elevational view of the back brace installed upon a human torso, of FIG. 1.

Referring to the drawings, there is shown in FIGS. 1 and 2 a back brace indicated generally at 10 according to one form of the invention, installed in supportive relationship to a human torso 11. This is shown from a rear view in FIG. 1 and a right side view in FIG. 2. Brace 10 includes a base 12 that has an upper edge 14 and a lower edge 15. The base 12 wraps around the mid-section of the individual encompassing the waist and regions above and below it. In particular, the base spans the small of the back and covers the regions of the iliac crests of the person as well.

As shown in FIGS. 3 and 4, the base 12 has right and left ends 17, 18 that come together at the front of the body. One end 17 has an inward facing 17A of hook and loop type fastening material of the type that adheres when pressed together, sold under the trademark VELCRO. The opposite end 18 has a corresponding opposite surface 18A that is outwardly facing for connection to the other end 17A to hold the base in tension about the torso 11.

Brace 10 includes an elastic strap assembly that works in conjunction with the base to offer support to the back. First and second elastic straps 23, 24 are fixed to the rear of the base 12 at a vertical reinforcing strip 26. The free ends of the straps 23, 24 are extendable around the torso parallel to the base 12. The free ends have inwardly facing fastening pads 27, 28 of adhering material of the type described. Side portions of the base have complementary sections 17B, 18B for attachment of the free ends of the straps 23, 24. With the base installed about a torso, the elastic straps 23, 24 are extended in tension partially around the torso and the ends 27, 28 fastened to the side segments 17B, 18B.

Base 12 is comprised primarily of a flexible and elastic band 30 of circumferentially stretchable material. A first accommodation panel 33 is fixed to the band 30 on one side thereof and is positioned to be in covering relationship to the region of the right iliac crest 16 of the individual when the base is installed on the individual. In like manner, a second accommodation panel 34 is fixed to the band 30 and is located at a position on band 30 so as to be in covering relationship to the region of the left iliac crest 19 of the individual.

Figure 5:
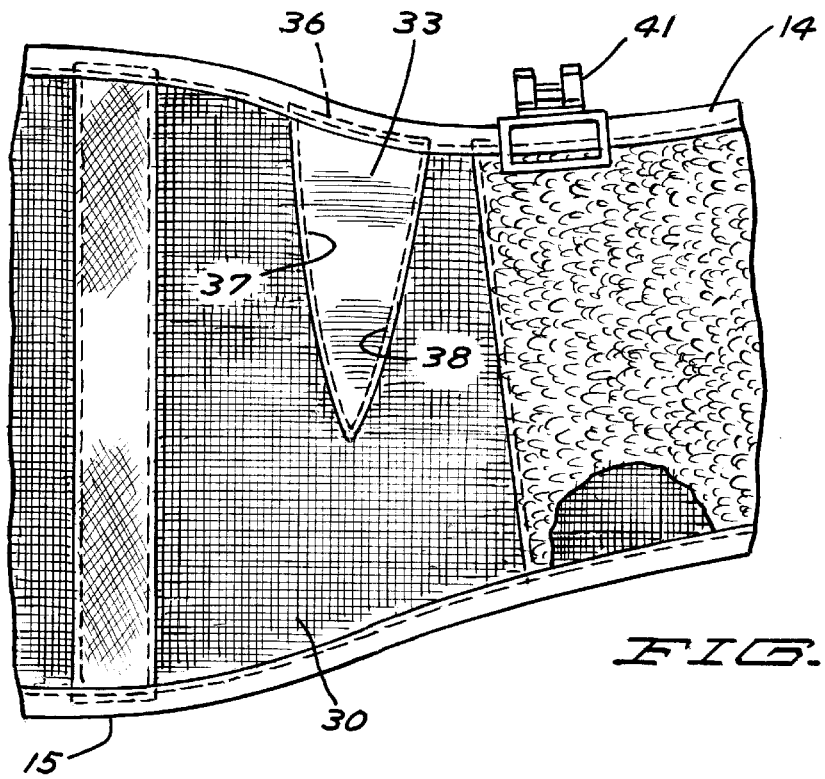
FIG. 5 is an enlarged view of a portion of the back brace of FIG. 1 showing the ilium panel.

Accommodation panels, 33, 34 are shaped alike. As shown in FIG. 5, the right panel 33 is generally triangular in shape. A top edge 36 of the panel is coextensive with a segment of the top edge 14 of the band 30. The panel 33 has a downwardly extended apex formed by side edges 37, 38. This apex is located between the upper edge 14 and the lower edge 15 of base 12. Panel 33 is formed of an inelastic material such as vinyl. Panel 33 is located on an elastic expanse of band 30.

Left panel 34 is symmetrically positioned on the base 12 so as to cover the region of the left iliac crest and is also formed of an inelastic material.

When base 12 is installed upon the torso 11 of the individual, the panels 33, 34 cover the regions of the right and left iliac crests. The band 30 of base 12 is placed in elastic tension. The panels 33,34 do not stretch. The panels accommodate the added dimension of the protuberances of the ilium. The elastic force of the band pulls the panels inwardly. This permits conformity of the base to the small of the back without a maximum portion of the tension being placed over the iliac crests. The band is also held securely in position. It does not ride up the waist.

In use, the base is installed upon the torso of the individual. If the individual is a work person requiring supplemental back support from time to time, the supplementary elastic straps 23, 24 are normally left unfastened. When the individual is about to perform strenuous work, the elastic straps are fastened.

Front and rear suspender clips 41, 42 are fixed to the upper edge 14 of base 12. The suspender clips releasably attach suspenders (not shown) if desired to assist in maintaining the position of the base 12 on the body.

Figure 6:
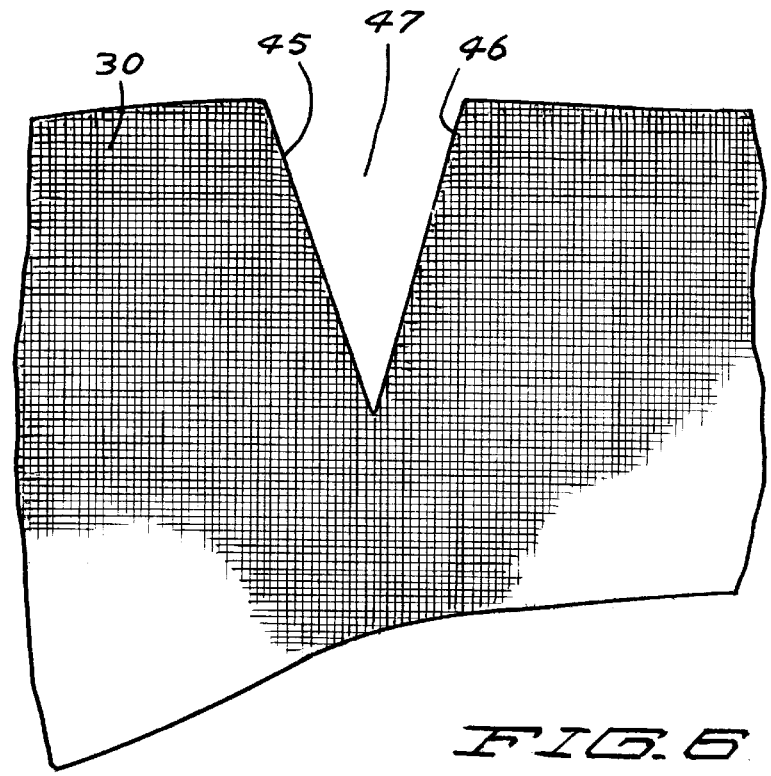
FIG. 6 is a schematic illustration of a first step of forming an accommodation panel in a back brace of the invention.
Figure 7:
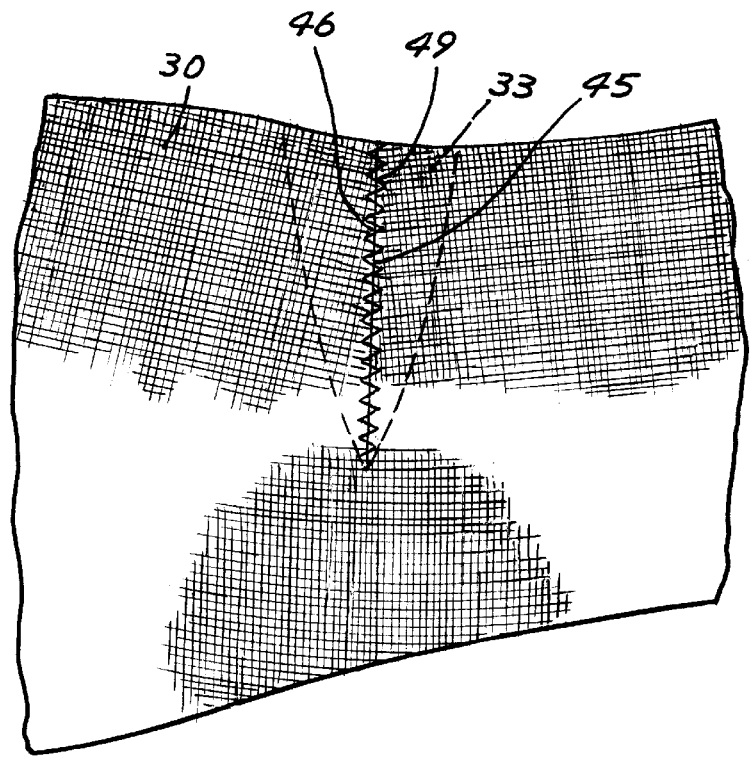
FIG. 7 is a schematic showing a second step of the formation of an accommodation panel.

A method of fabricating and attaching an accommodation panel is illustrated in FIGS. 6 and 7. An elastic band 30 used for fabrication of the brace is provided with a notch or cut out portion by cutting sides 45, 46 in a triangular shape, leaving a notch 47. This is shown in FIG. 6. In FIG. 7 the notch 47 is closed. This is accomplished by bringing the edges 45, 46 together and fastening them with stitching to form a seam 49. This can create a small pocket or bulge in the band 30. As shown in phantom, an accommodation panel 33 is sewn over the seam 49. This becomes a place for the accommodation of the iliac crest of the person.

Figure 8:
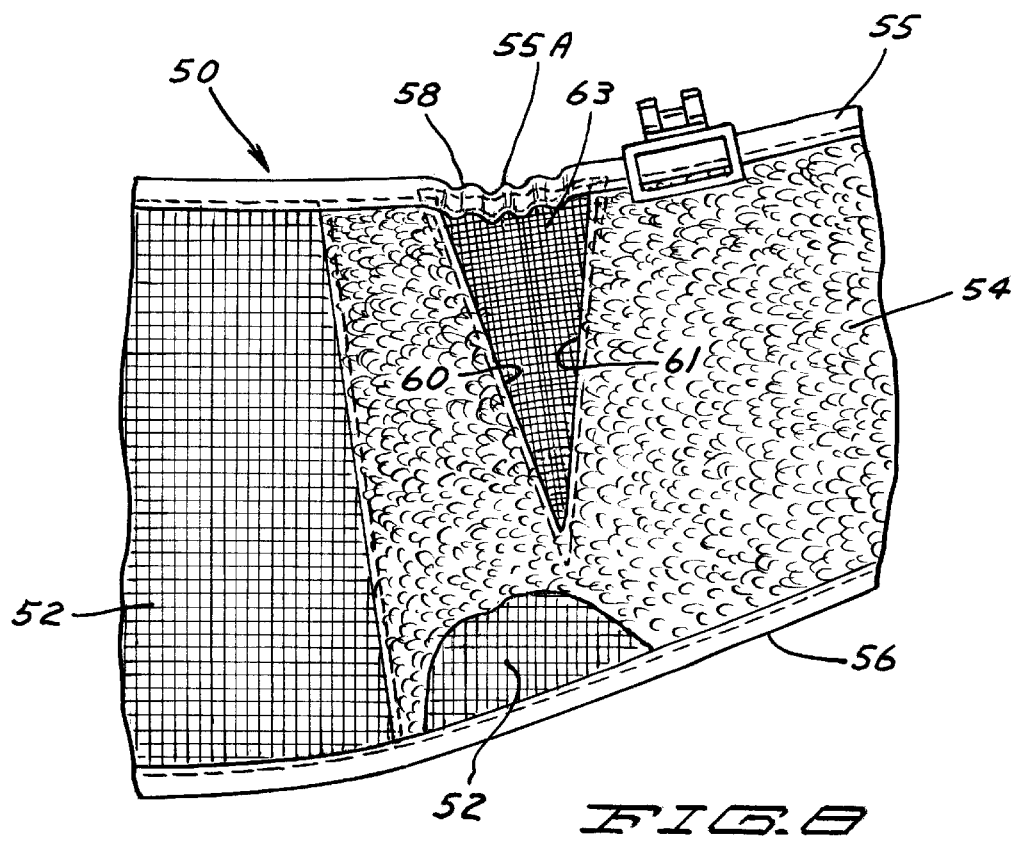
FIG. 8 is an enlarged view like that of FIG. 5 but showing another form of the back brace.

FIG. 8 shows a portion of a back brace 50 according to a second form of the invention which is similar to the portion of the back brace shown in FIG. 5. This includes a side segment of the back brace on the right side of the person in covering relationship to the region of the iliac crest on the right side.

The back brace 50 includes an elongate base 52 configured in like fashion to the base of the earlier embodiment to wrap around the torso of a person. However, the base 52 is formed on a inelastic material. For example, it can be a vinyl mesh material which will be strong and yet allow air circulation. A segment of adhering material 54 can be attached to the base 52 to attach support straps of the type earlier described. The base 52 has an upper edge with edging 55, and a bottom edge 56.

An iliac relief panel 58 is located on the base 52. The panel 58 is located in the same position as the panels earlier described but with respect to the first embodiment. The relief panel 58 covers the region on a person of the right iliac crest. The base 52 is positioned on the person so that the upper edge 55 is located above the iliac crest, and the lower edge 56 is located beneath it. The relief panel 58 is generally triangular in shape. It is located in a cut out triangular portion of the base 52 defined by edges 60, 61. The panel 58 is formed of an elastic material 63. The material 63 is stretchable in a circumferential direction. The edges 60, 61 are sewn securely to the base 52.

The relief panel 58 is generally triangular in shape as earlier disclosed. One edge is co-extensive with the upper edge of the base 52. The upper edging 55 is bunched as shown at 55A at that region co-extensive with the top edge of the panel 58. This permits stretching of the panel 58 uninhibited by the edging 55. Alternatively, the edging 55 or at least a portion of it, could be elastic as well in order to stretch with the panel 58.

In use of the form of the invention shown in FIG. 8, the base 52 is installed about the waist of a person. The upper edging 55 is located above the iliac crest of the person, and the lower edging 56 is located beneath. The right panel 58 and the left panel which is substantially identical (not shown) span the region of the iliac crests. The elastic panels stretch over the crest. The protuberance of the iliac crest is accommodated by the elastic panels. This permits the remainder of the base 52 to be snugly engaged with the body and in particular the small of the back. In addition, it secures the brace 50 more securely to the person and prevents riding up of the brace. This closer conformance to the back lends a great deal more support to the sacral area.

While certain preferred embodiments of the invention have been described, it will be apparent that deviations can be had without departing from the scope and spirit of the invention.

I claim:

1. A back brace for installation about the waist of a wearer in spanning and supportive relation to the lumbar region of the back, and covering the iliac crests of the individual on the right and left sides, comprising:

an elongate band configured to be wrapped around the waist of a wearer, having first and second ends that come together at the front of the wearer, and releasable fastening means on the first and second ends to fasten them together and place the band in tension about the torso of the wearer;

said band having an upper edge for encircling the waist of the wearer at a position located above the iliac crests, and a lower edge for location beneath the iliac crests of the wearer;

said band formed of an elastic material;

right and left iliac accommodation panels fixed to the band position on the band to be located in covering relationship to the regions of the right and left iliac crests when the band is installed on a wearer;

each panel being generally triangular in shape, having a top edge co-extensive with a segment of the upper edge of the band, and a downwardly directed apex that terminates above the lower edge of the band;

said panels being formed of an inelastic material.

2. The back brace of claim 1 wherein:

in the region of each panel, a v-shaped notch has been cut out from the band, and the remaining edges sewn together to form a seam, and said inelastic panel being fastened in covering relationship to the seam.

3. The brace of claim 2 wherein:

one end of the band has a inwardly facing surface of adhering material, the other end of the band has an outwardly facing surface of adhering material for releasable attachment to the inwardly facing surface of the first end.

4. The back brace of claim 2 including:

an elastic strap assembly including first and second elastic straps fixed to the band in the vicinity of the back of the wearer, extendable around to the vicinity of the front of the wearer, and means on the free ends of the elastic support straps for fastening them to the band in tension.

5. A back brace for installation about the waist of a wearer in spanning and supportive relation to the lumbar region of the back, and covering the iliac crests of the individual on the right and left sides, comprising:

an elongated elastic band configured to be wrapped around the waist of a wearer, having first and second ends that come together at the front of the wearer, and releasable fastening means on the first and second ends to fasten them together and place the band in tension about the torso of the wearer;

said band having an upper edge for encircling the waist of the wearer at a position located above the iliac crests, and a lower edge for location beneath the iliac crests of the wearer;

right and left iliac accommodation panels fixed to the band positioned on the band to be located in covering relationship to the regions of the right and left iliac crests when the band is installed on a wearer;

each panel being of suitable size and shape to cover the iliac crest and the region immediately surrounding it;

said panels being formed from an inelastic material.

6. The back brace of claim 5 wherein:

in the region of each panel, a v-shaped notch has been cut out from the band, and the remaining edges sewn together to form a seam, and said inelastic panel being fastened in covering relationship to the seam.

7. The back brace of claim 6 wherein:

one end of the band has a inwardly directed surface of adhering material, the other end of the band has an outwardly facing surface of adhering material for releasable attaching to the inwardly facing surface of the first end.

8. The back support brace of claim 6 including:

an elastic strap assembly including first and second elastic straps fixed to the band in the vicinity of the front of the wearer, and means on the free ends of the elastic support straps for fastening them to the base in tension.

* * * * *